(12) United States Patent
Kwon et al.

(10) Patent No.: US 9,970,856 B2
(45) Date of Patent: May 15, 2018

(54) VEHICULAR DUST SENSOR

(71) Applicants: Hyundai Motor Company, Seoul (KR); TRUWIN, Daejeon (KR); Hanon Systems, Daejeon (KR)

(72) Inventors: Dong Ho Kwon, Bonghwa-eup (KR); Gee Young Shin, Suwon-si (KR); Kwang Woon Cho, Yongin-si (KR); Jun Ho Choi, Daejeon (KR); Sang Ho Oh, Daejeon (KR); Chae Geun Lim, Daejeon (KR); Ji Min Lee, Jeonju-si (KR); Du Yeol Kim, Daejeon (KR); Young Hu Lee, Cheongju-si (KR)

(73) Assignees: Hyundai Motor Company, Seoul (KR); TRUWIN, Daejeon (KR); Hanon Systems, Daejeon (KR)

( * ) Notice: Subject to any disclaimer, the term of this patent is extended or adjusted under 35 U.S.C. 154(b) by 0 days. days.

(21) Appl. No.: 15/291,946

(22) Filed: Oct. 12, 2016

(65) Prior Publication Data
US 2017/0276592 A1     Sep. 28, 2017

(30) Foreign Application Priority Data
Mar. 25, 2016     (KR) .......................... 10-2016-0035765

(51) Int. Cl.
*G01N 21/00*     (2006.01)
*G01N 15/14*     (2006.01)

(52) U.S. Cl.
CPC ..... *G01N 15/1425* (2013.01); *G01N 15/1429* (2013.01)

(58) Field of Classification Search
CPC .............. G01N 15/1429; G01N 21/53; G01N 2021/4711; G01F 1/6842; G01P 5/10; G08B 17/107
USPC .......................... 356/343, 339, 437, 335–337
See application file for complete search history.

(56) References Cited

U.S. PATENT DOCUMENTS

| | | | | |
|---|---|---|---|---|
| 4,226,533 A | * | 10/1980 | Snowman ................. | G01V 8/12 250/574 |
| 4,266,219 A | * | 5/1981 | Foster .................. | G08B 17/103 250/574 |
| 5,008,559 A | * | 4/1991 | Beyersdorf .......... | G08B 17/107 250/575 |
| 5,670,947 A | * | 9/1997 | Nagashima .......... | G08B 17/107 250/564 |

(Continued)

FOREIGN PATENT DOCUMENTS

| | | |
|---|---|---|
| JP | 2007-121145 A | 5/2007 |
| JP | 2007-218587 A | 8/2007 |

(Continued)

*Primary Examiner* — Isiaka Akanbi
(74) *Attorney, Agent, or Firm* — Morgan, Lewis & Bockius LLP (57) ABSTRACT

A vehicular dust sensor may include a case having an inner space, a light source module disposed in the inner space of the case, and irradiating an air passage with light, the air passage being provided in the light source module for introduction and pass of air and dust, a condensing lens to collect light, emitted from the light source module and scattered by dust in air in the air passage, a light receiving module receiving the scattered light collected by the condensing lens to output an electric signal corresponding to a dust concentration, and an inner housing disposed in the inner space of the case to form the air passage.

13 Claims, 8 Drawing Sheets

(56) References Cited

U.S. PATENT DOCUMENTS

| | | | | |
|---|---|---|---|---|
| 6,184,537 B1* | 2/2001 | Knox | .................... | G01N 21/53 |
| | | | | 250/574 |
| 6,479,833 B1* | 11/2002 | Pfefferseder | ......... | G08B 17/107 |
| | | | | 250/573 |
| 6,778,091 B2* | 8/2004 | Qualey, III | .......... | G08B 17/107 |
| | | | | 250/574 |
| 7,440,100 B2* | 10/2008 | Siemens | ................ | G01N 21/53 |
| | | | | 356/335 |
| 7,551,277 B2* | 6/2009 | Cole | .................... | G01F 1/6842 |
| | | | | 356/335 |
| 2015/0268159 A1* | 9/2015 | Tabaru | ................... | G01N 21/39 |
| | | | | 356/437 |

FOREIGN PATENT DOCUMENTS

| KR | 20-0333726 Y1 | 11/2003 |
|---|---|---|
| KR | 20-0381009 Y1 | 4/2005 |
| KR | 10-0539310 B1 | 1/2006 |
| KR | 10-2008-0038151 A | 5/2008 |
| KR | 10-2011-0080646 A | 7/2011 |

\* cited by examiner

AIR (CONTAINING DUST)

VEHICULAR DUST SENSOR

CROSS-REFERENCE TO RELATED APPLICATION

The present application claims priority to Korean Patent Application No. 10-2016-0035765, filed Mar. 25, 2016, the entire contents of which is incorporated herein for all purposes by this reference.

BACKGROUND OF THE INVENTION

Field of the Invention

Various aspects of the present invention relate to a vehicular dust sensor. More particularly, to a vehicular dust sensor capable of preventing deterioration of sensor performance or malfunction thereof due to deposition of dust in a case, or lens contamination and disturbance light introduced from the outside, and of resolving output abnormality from a light emitting diode and the resultant deterioration of sensor performance.

Description of Related Art

In general, optical sensors are widely used as dust sensors to measure the amount and concentration of fine dust contained in air, and particularly there is known a light scattering method of detecting the amount of light scattered through dust in air.

Such a light scattering type dust sensor includes a light source module having a light emitting element such a Light Emitting Diode (LED), a light receiving module having a light receiving element such as a Photo Diode (PD), and a lens for collecting light scattered by dust in air.

The light source part, the light receiving part, and the lens are installed in a case of the dust sensor. In this case, the case has an inlet port for introducing air which may contain dust.

When the LED of the dust sensor irradiates an illumination region in the case with light, the light is scattered by dust in air, i.e. dust particles, introduced into the case. In this case, the intensity (or amount) of the scattered light is proportional to the concentration of the dust particles in the air.

Accordingly, the dust sensor collects the light scattered by the dust particles in the air using the lens, and receives the collected light using the PD to output electric signals corresponding to the dust concentration.

However, the performance of the conventional dust sensor may easily deteriorate due to the deposition of dust in the case.

Particularly, the sensor may malfunction due to the contamination of the condensing lens therein, and the amount of light from the LED may be reduced due to the continuous use of the sensor and the sensitivity of the sensor may therefore deteriorate.

In addition, visible light or ultraviolet light may be easily introduced into the case through the air inlet port therein, and the light introduced from the outside acts as disturbance light which is a major cause of the malfunction of the sensor.

The information disclosed in this Background of the Invention section is only for enhancement of understanding of the general background of the invention and should not be taken as an acknowledgement or any form of suggestion that this information forms the prior art already known to a person skilled in the art.

BRIEF SUMMARY

Various aspects of the present invention are directed to providing a vehicular dust sensor capable of preventing deposition of dust in a case or lens contamination in order to prevent deterioration of sensor performance or malfunction thereof.

Additionally, various aspects of the present invention are directed to providing a vehicular dust sensor capable of blocking introduction of external light into an illumination region in a case in order to prevent the sensor from malfunction due to the external light.

Furthermore, various aspects of the present invention are directed to providing a vehicular dust sensor capable of detecting output abnormality from a light emitting diode as a light emitting element in order to resolve the output abnormality from the light emitting diode and the resultant deterioration of sensor performance.

A vehicular dust sensor in a case having an inner space, a light source module disposed in the inner space of the case, and irradiating an air passage with light, the air passage being provided in the light source module for introduction and pass of air and dust, a condensing lens to collect light, emitted from the light source module and scattered by dust in air in the air passage, a light receiving module receiving the scattered light collected by the condensing lens so as to output an electric signal corresponding to a dust concentration, and an inner housing disposed in the inner space of the case to form the air passage.

The air passage may be a linear air passage formed such that air and dust are introduced into and easily discharged from the air passage, and both end openings of the linear air passage may be entry ports for introduction and discharge of air and dust.

The air passage may be a passage having a constant cross-sectional shape.

The air passage may be a passage having a circular cross-sectional shape.

The light source module may be an infrared light source module to emit infrared light, and an infrared-passing filter may be disposed between the condensing lens and the light receiving part.

The inner housing may be formed with a groove-shaped air guide portion for forming the air passage, and an inner surface of one side portion of the case may be formed with a groove-shaped linear air guide portion for forming the air passage in a combined state with the air guide portion of the inner housing.

A first light passage having a structure that is branched from the air passage by the inner housing may be formed, and a light emitting element of the light source module may be disposed in the first light passage, so that the light emitting element irradiates the air passage with light through the first light passage.

A second light passage having a structure that is branched from the air passage by the inner housing may be formed, and a light receiving element of the light receiving module and the condensing lens may be disposed in the second light passage, so that light scattered in the air passage may be collected by the condensing lens while passing through the second light passage, and may be then input to the light receiving element.

A beam splitter, which divides at least a portion of light emitted from a light emitting element of the light source module and passes the remainder of light therethrough so as to irradiate the air passage, and a light sensor, which detects the light divided by the beam splitter to output an electric signal according to an amount of the divided light may be disposed in front of the light emitting element of the light source part, and a controller may determine whether light output from the light emitting element is abnormal based on the signal output from the light sensor.

The light sensor may be a photo diode which receives the divided light to output an electric signal.

When the amount of the light divided by the beam splitter is beyond a predetermined normal range, the controller may determine that the light output from the light emitting element is abnormal based on the signal output from the light sensor, and the controller may regulate a voltage applied to the light emitting element such that the amount of the light divided by the beam splitter is in the normal range, and may control the light output from the light emitting element.

External light blockages, which block introduction of external light while passing air and dust therethrough, may be disposed to both end openings of the air passage as entry ports for air and dust.

Each of the external light blockages may be a light-blocking cap, the light-blocking cap including a blockage plate disposed to be spaced apart from each opening of the air passage and to cover the opening, and a plurality of pillars supporting the blockage plate in a state in which the blockage plate is spaced apart from the opening.

Each of the external light blockages may include a tubular body inserted into and disposed to each end of the air passage such that an outer surface of the tubular body comes into contact with an inner surface of the air passage, and shield walls fixedly disposed on an inner surface of the tubular body so as to form a passage for introduction of dust and air while blocking external light.

Each of the shield walls may be obliquely disposed on the inner surface of the tubular body.

The shield walls may be fixedly disposed in opposite sides on the inner surface of the tubular body so as to form the passage for introduction of dust and air in a zigzag form while blocking light, and may be disposed at intervals in a longitudinal direction of the air passage so as to form a cross structure.

The air passage may be a circular cross-sectional passage, and the tubular body has a circular tubular shape, and each of the shield walls may have a semicircular shape.

It is understood that the term "vehicle" or "vehicular" or other similar terms as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g., fuel derived from resources other than petroleum). As referred to herein, a hybrid vehicle is a vehicle that has two or more sources of power, for example, both gasoline-powered and electric-powered vehicles.

The methods and apparatuses of the present invention have other features and advantages which will be apparent from or are set forth in more detail in the accompanying drawings, which are incorporated herein, and the following Detailed Description, which together serve to explain certain principles of the present invention.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in module by the particular intended application and use environment.

DETAILED DESCRIPTION

Reference will now be made in detail to various embodiments of the present invention(s), examples of which are illustrated in the accompanying drawings and described below. While the invention(s) will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the invention as defined by the appended claims.

First, the configuration of a known light scattering type dust sensor will be described with reference to FIG. 1 for comparison with the configuration of the present invention.

Figure 1:
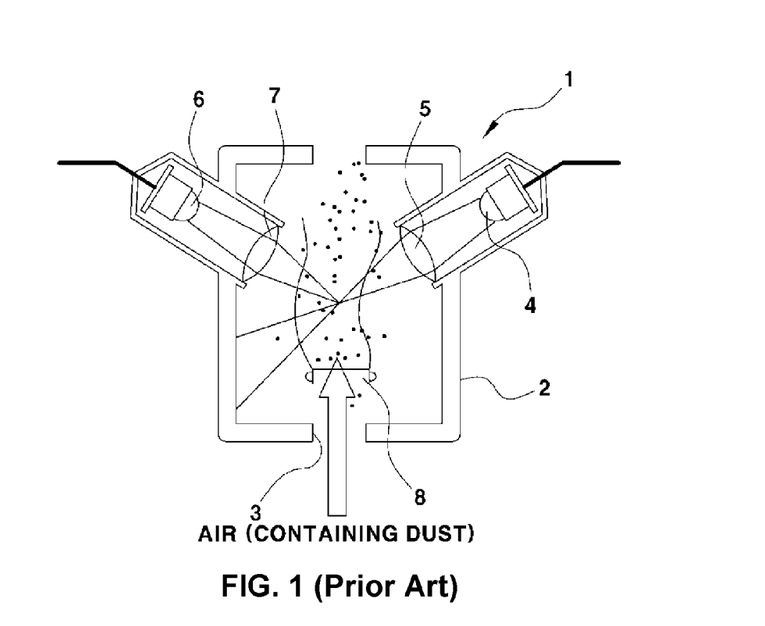
FIG. 1 is a view illustrating the configuration of a known light scattering type dust sensor.

As illustrated in FIG. 1, a light scattering type dust sensor 1 includes a light source module having a light emitting element such a Light Emitting Diode (LED) 4, a light receiving module having a light receiving element such as a Photo Diode (PD) 6, and a condensing lens 7 to collect light scattered by dust in air.

The LED 4, the PD 6, and the condensing lens 7 are installed in a case 2 of the dust sensor 1, and the case 2 has an inlet port 3 through which air and dust may be introduced.

When the LED 4 as the light emitting element of the known dust sensor 1 irradiates an illumination region in the case 2 with light, the light is scattered by dust in air, i.e. dust particles, introduced into the case. In this case, the intensity (or amount) of the scattered light is proportional to the concentration of the dust particles in the air.

Accordingly, the dust sensor 1 collects the light scattered by the dust particles in the air using the condensing lens 7, and receives the collected light using the PD 6 as the light receiving element to output electric signals corresponding to the dust concentration.

In addition, the known dust sensor 1 may include a heater 8 installed in the lower portion of the case 2, as illustrated in the FIG. 1. The dust particles in the case 2 are lifted by heat generated by the heater 8, and the light radiated to the illumination region is scattered by the lifted dust particles when the particles pass through the illumination region.

Referring to FIG. 1, the known dust sensor 1 has a structure in which dust introduced into the case 2 may be easily deposited, but does not have a structure that may prevent lenses 5 and 7 from being contaminated due to dust deposition or dust.

In addition, external light may be easily introduced into the case 2 through the inlet port 3 for the introduction of air containing dust. However, the dust sensor does not have a structure for preventing the introduction of external light.

Accordingly, various embodiments of the present invention provide the configuration and structure of a sensor capable of preventing dust from being deposited in a case while the dust may be easily discharged to the outside of the case, and of effectively blocking the introduction of external light into the case.

Figure 2:
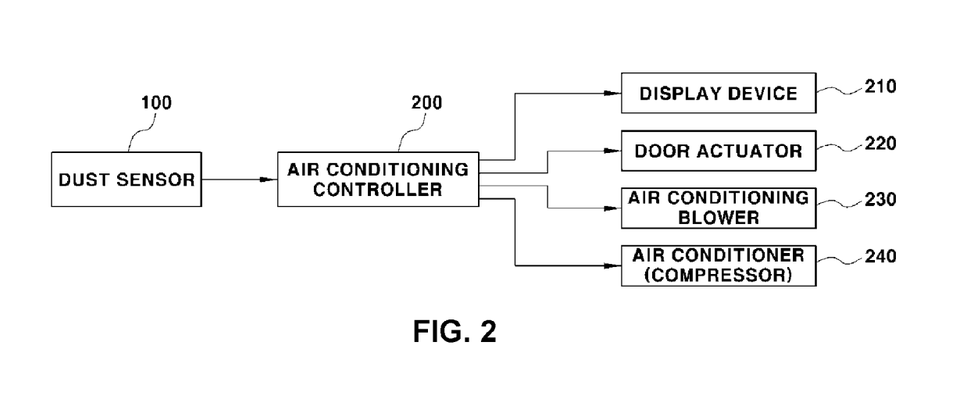
FIG. 2 is a diagram illustrating the use of a dust sensor according to various embodiments of the present invention, and illustrating a vehicle system for performing air conditioning according to a dust concentration.

A dust sensor according to various embodiments of the present invention may be a vehicular dust sensor which measures the concentration of dust contained in air in a vehicle. FIG. 2 is a diagram illustrating the use of the dust sensor according to various embodiments of the present invention, and illustrating a vehicle system for performing air conditioning according to a dust concentration.

The dust sensor, which is designated by reference numeral 100, according to various embodiments of the present invention is disposed at a predetermined position inside or outside a vehicle. The dust sensor 100 measures the concentration of dust in air to output signals in response to the measured values.

The signals output from the dust sensor 100 are transmitted to an air conditioning controller 200, the air conditioning controller 200 outputs control signals indicative of a current concentration state from the dust concentration information obtained by the dust sensor 100, and a display device 210, which receives the control signals, displays an alarm state for each stage to warn a driver of it.

In addition, when a dust concentration over a certain level is detected by the dust sensor 100 according to automatic logic of removal of dust, the air conditioning controller 200 outputs control signals for changing to an inside air mode, increasing the number of operation stages of an air conditioning blower 230, and turning on an air conditioner 240. Thus, in the vehicle, it is changed to the inside air mode (an air intake door is changed to a position of the inside air mode by driving a door actuator 220), the number of operation stages of the air conditioning blower 230 is increased, and the air conditioner 240 is operated (an air conditioning compressor is driven).

Figure 3A:
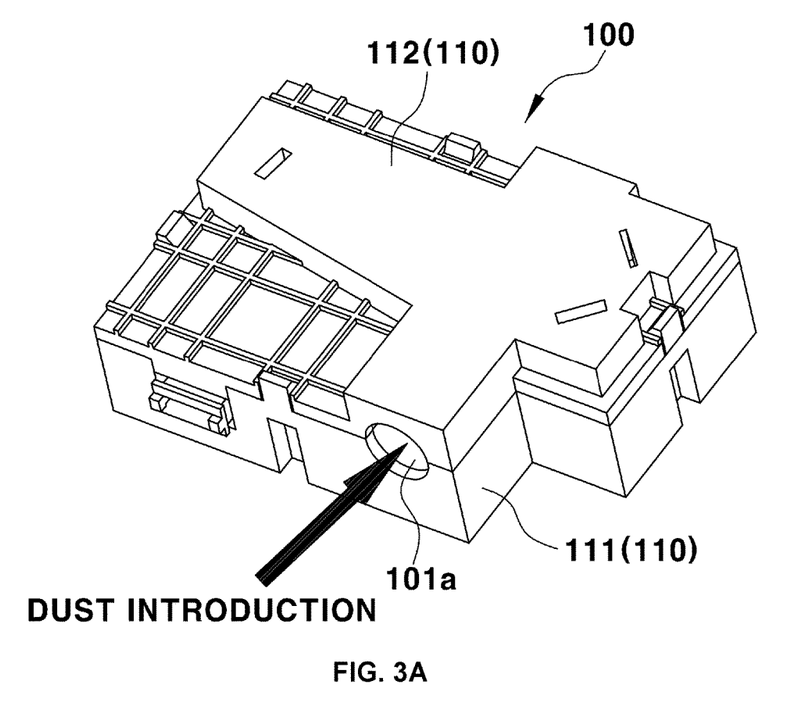
FIG. 3A and FIG. 3B are assembled perspective views illustrating the dust sensor according to various embodiments of the present invention.
Figure 3B:
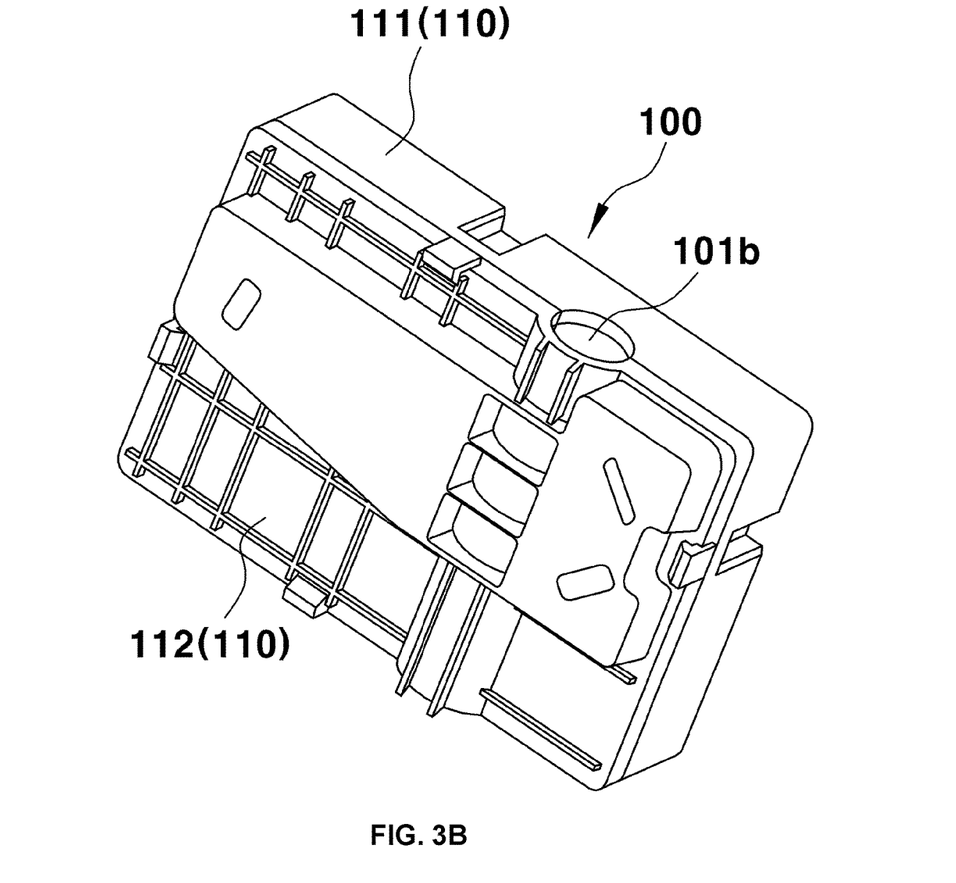
Figure 4:
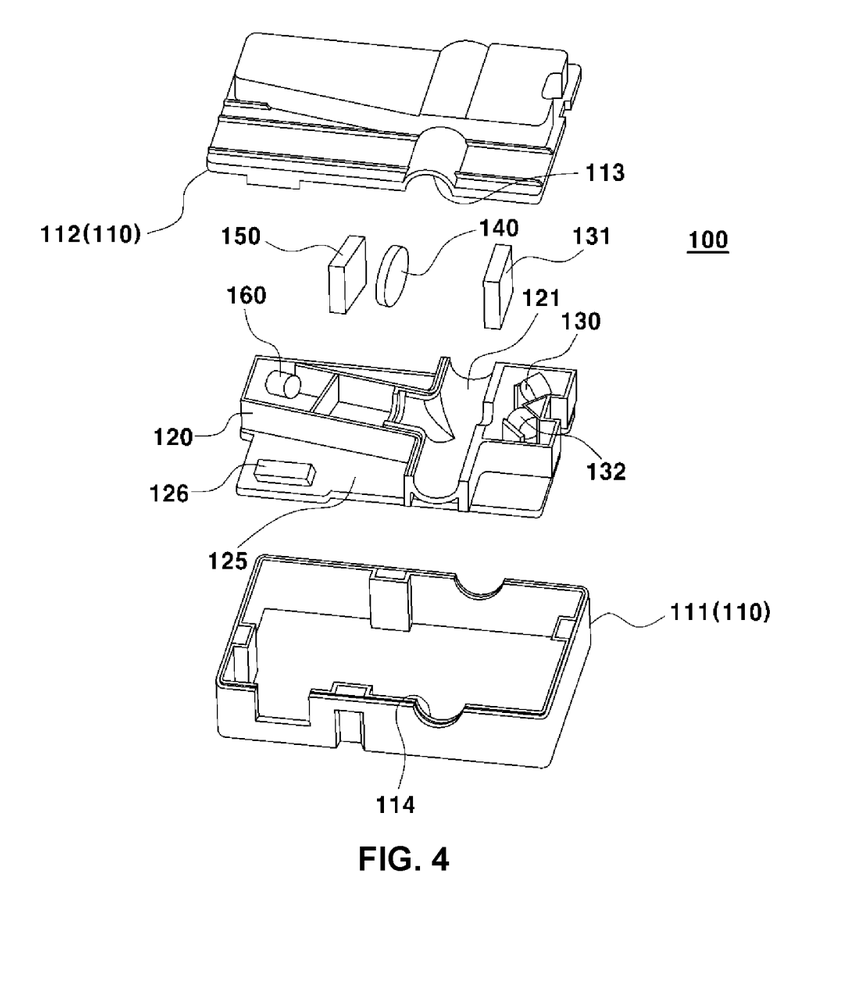
FIG. 4 is an exploded perspective view illustrating the dust sensor according to various embodiments of the present invention.
Figure 5:
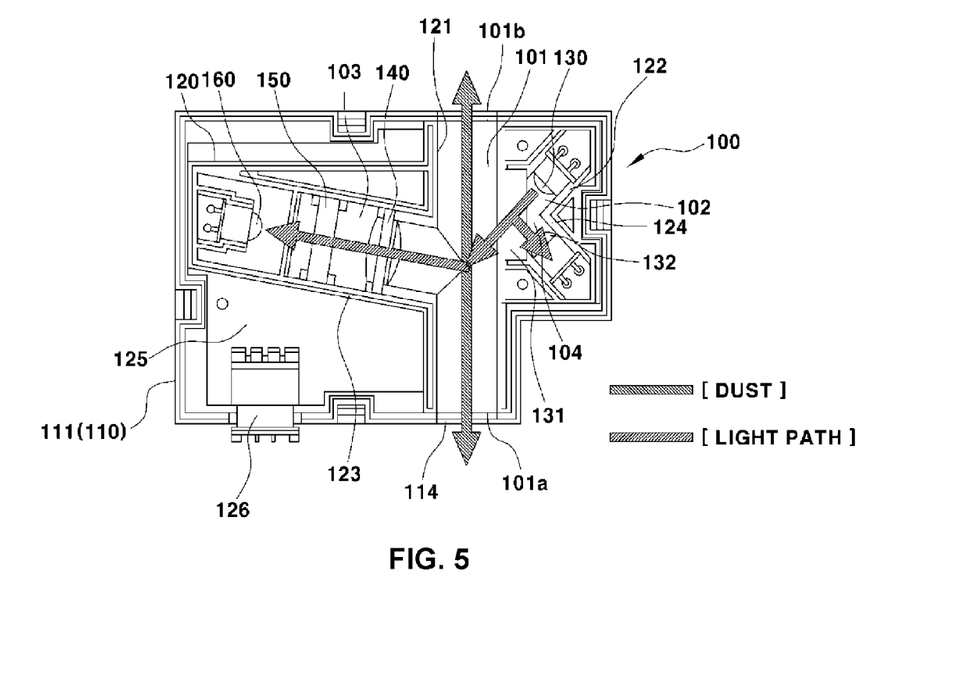
FIG. 5 is a view illustrating the inner configuration of the dust sensor according to various embodiments of the present invention.

FIG. 3 is an assembled perspective view illustrating the dust sensor according to various embodiments of the present invention. FIG. 4 is an exploded perspective view illustrating the dust sensor according to various embodiments of the present invention. FIG. 5 is a view illustrating the inner configuration of the dust sensor according to various embodiments of the present invention.

The examples in FIGS. 3A and 3B illustrate a slight difference in the external appearance and shape of the dust sensor, but there is no difference in the configuration or technical feature thereof.

For reference, FIG. 4 is an exploded perspective view of the dust sensor illustrated in FIG. 3A, and FIG. 5 is a view illustrating the inner configuration of the dust sensor illustrated in FIG. 3A.

The dust sensor 100 according to various embodiments of the present invention may be an optical sensor for measuring the concentration of dust in air, and more particularly be a vehicular dust sensor using a light scattering method of detecting the amount (or intensity) of light scattered by dust in air to measure the concentration of the dust in the air.

In particular, the dust sensor 100 has a configuration and a structure capable of discharging dust introduced into a case 110 to the outside thereof so as to prevent the dust from being deposited in the case and to reduce the contamination of a condensing lens 140, and of blocking the introduction of external light into the case so as to prevent the malfunction of the sensor due to the external light.

First, the dust sensor 100 according to various embodiments of the present invention includes a case 110 having an inner space, and an inner housing 120 that is disposed in the inner space of the case 110 and forms, together with one side portion of the case, an air passage (designated by reference numeral 101 in FIG. 5) through which dust passes and light passages (designated by reference numerals 102 and 103 in FIG. 5) through which light passes.

Here, the case 110 includes a case body 111 which is opened at one surface thereof and has an inner space defined by a sidewall and a bottom, and a cover 112 assembled thereto so as to cover one surface of the case body 111. The air passage 101 and the light passages 102 and 103 are formed by the cover 112 assembled to the case body 111 and the inner housing 120 installed in the inner space of the case.

The case 110 including the case body 111 and the cover 112 includes the inner housing 120, and serves to protect sensor components such as an LED 130 as a light emitting element, a PD 160 as a light receiving element, and a condensing lens 140 as an optical element for optical conversion.

In addition, the inner housing 120 is a portion in which the sensor components such as the LED 130, the PD 160, and the condensing lens 140 are fixedly disposed, and serves to form the air passage 101 and the light passages 102 and 103.

In various embodiments, the inner housing 120 has a groove-shaped linear air guide portion 121 which forms the air passage 101. In this case, a groove-shaped linear air guide portion 113 is formed at a position corresponding to the air guide portion of the inner housing in one side portion of the case 110, i.e. in the inner surface of the cover 112.

The air guide portion 121 of the inner housing 120 and the air guide portion 113 of the cover 112 form one linear air passage 101 in the state in which the inner housing 120 and the cover 112 are assembled to each other. In various embodiments, the linear air passage 101 may be a passage having a constant cross-sectional shape, e.g. a circular cross-sectional shape (see FIG. 5).

That is, one linear air passage 101 having a cylindrical shape is formed in the state in which the air guide portion 121 of the inner housing 120 and the air guide portion 113 of the cover 112 are assembled to each other.

In this case, both end openings 101a and 101b of the air passage 101 formed by both air guide portions 113 and 121 are an inlet for introduction of air and dust and an outlet for discharge of air and dust.

That is, both end openings 101a and 101b of the air passage 101 are the inlet and at the same time the outlet for introduction and discharge of dust. Dust introduced into the linear air passage 101 is discharged through the air passage. In particularly, dust receives light emitted through a first light passage 102 from the LED 130 when the dust passes through an illumination region in the air passage 101.

In addition, the sidewall of the case body 111 may have circular grooves 114 formed at both end positions of the air passage 101 so as not to close both end openings 101a and 101b (the inlet and outlet for dust) of the air passage.

Thus, the path of air and dust is set as the linear inner path of the air passage 101 formed by the inner housing 120 in the case 110, and the concentration of dust may be measured while air containing the dust passes through the liner air passage 101.

When the dust sensor includes the linear air passage 101 for the pass of air and dust by forming the linear air guide portion 121 in the inner housing 120, dust may be easily discharged from the dust sensor 100. Consequently, it is possible to effectively prevent dust deposition in the sensor and lens contamination due to dust, and to prevent deterioration of sensor performance due to dust deposition or contamination.

A portion in the air passage 101 is set as an illumination region, and a light source module having a light emitting element such an LED 130, a light receiving module having a light receiving element such as a PD 160, and a condensing lens 140 to collect light scattered by dust in air in the air passage 101 are fixedly disposed in the inner housing 120.

In addition, the inner housing 120 has light guide portions 122 and 123 which form the light passages 102 and 103 together with one side portion of the case 110, i.e. the cover 112.

Here, the light guide portions include a first light guide portion 122 which forms a first light passage 102 and a second light guide portion 123 which forms a second light passage 103.

The first light passage 102 is a light passage in which light emitted from the LED 130 of the light source module passes toward the air passage 101, and the second light passage 103 is a light passage in which light scattered by dust in air in the air passage 101 passes toward the PD 160.

The first and second light guide portions 122 and 123 of the inner housing 120 form the first and second light passages 102 and 103 together with the inner surface of the cover 112 which is one side portion of the case 110. In this case, both the first and second light passages 102 and 103 may be obliquely formed to have a predetermined angle of inclination to the air passage 101.

Both the first and second light passages 102 and 103 have a passage structure that is obliquely branched from the air passage 101.

In addition, the LED 130 is fixedly disposed in the first light passage 102, and a beam splitter 131, which reflects at least a portion of light emitted from the LED 130 while passing the remainder therethrough, is disposed in front of the LED 130 in the first light passage 102, at the outlet of the first light passage 102.

In various embodiments of the present invention, the light source module may include a configuration for emitting and radiating infrared light, i.e. an infrared LED 130. In this case, the infrared light emitted from the infrared LED 130 is light used to detect the concentration of dust in air (light radiated toward dust).

In addition, a light receiving passage 104 having a structure that is obliquely branched from the first light passage 102 is formed, and the light receiving passage 104 is a passage formed by the assembly of the light receiving guide portion 124 formed in the inner housing 120 and the cover 112.

A separate light sensor 132, which detects light reflected by the beam splitter 131 to output electric signals, is disposed in the light receiving passage 104, and the light sensor 132 may include the PD 160 which receives light reflected by the beam splitter 131 through the light receiving passage 104 to output electric signals.

The light sensor 132 is a sensor which determines whether the LED 130 of the light source module is normally operated, particularly whether light for detecting dust concentration is normally emitted from the LED 130.

To this end, the light sensor 132 receives light divided by the beam splitter 131 to detect the amount (or intensity) of the divided light. When an electric signal according to the amount of the divided light is output from the light sensor 132, the electric signal is input to a controller (e.g. an air conditioning controller) so that the controller determines whether the light output from the LED 130 is normal.

In this case, when the amount of the divided light is beyond a predetermined normal range, the controller determines that the light output from the LED 130 is abnormal. Thus, the controller outputs a control signal for regulating a voltage applied to the LED 130 such that light is normally output from the LED 130.

For example, since the light output from the LED 130 is lack when the amount of the divided light is below the normal range, the controller outputs a correction control signal for increasing a voltage applied to the LED 130. As a result, the light output from the LED 130 is increased while the amount of light divided by the beam splitter 131 is within the normal range.

The light sensor 132 is used to determine whether the light source module is normally operated and is also used to correct the output from the light source part, i.e. to control and correct the voltage applied to the LED 130 such that light is normally emitted from the LED 130 without abnormality.

Meanwhile, the PD 160, which is the light receiving element used as a sensor for detecting dust concentration, is installed in the second light passage 103, and the condensing lens 140 which collects light scattered by dust is installed in front of the PD 160.

In various embodiments, when the infrared LED 130 is used as the LED 130 of the light source part, an infrared-passing filter 150 may be disposed in the second light passage between the PD 160 and the condensing lens 140.

The infrared-passing filter 150 is installed in the second light passage 103 so as to block visible light and ultraviolet light in the light introduced from the outside of the sensor. Thus, it is possible to prevent the dust sensor 100 from malfunction by blocking visible light and ultraviolet light to the PD 160.

As a result, when infrared light is emitted from the infrared LED 130 of the light source part, infrared light passing through the beam splitter 131 reaches the illumination region of the air passage 101, and the infrared light in the illumination region of the air passage 101 is scattered by dust particles introduced into the air passage 101 through both end openings 101a and 101b.

In addition, the infrared light scattered by the dust particles is collected by the condensing lens 140, and is then received by the PD 160 through the infrared-passing filter 150, so that the PD 160 outputs an electric signal corresponding to the amount (or intensity) of the received infrared light.

In this case, the electric signal output from the PD 160 is converted into a predetermined signal in a circuit portion of a PCB 125 in the dust sensor 100, and is finally output through a connector pin 126 of the dust sensor 100. The signal, which is finally output from the dust sensor 100, is then input to the controller.

The signal output from the dust sensor 100 is a signal indicative of a current concentration of dust in air. When the dust concentration is above a predetermined level, the controller (e.g. the air conditioning controller) performs air conditioning control in order to remove dust in the vehicle interior, based on the signal output from the dust sensor 100.

In this case, in order to control air conditioning according to dust concentration, i.e. to perform air conditioning control for removing dust in the vehicle interior, the controller may be set to change to an inside air mode, increase the number of operation stages of an air conditioning blower, and turn on an air conditioner.

The PCB 125 may be integrally attached to the inner housing 120, and the connector pin 126 may be integrally mounted to the PCB 125.

In addition, the circuit portion of the PCB 125 may convert the electric signal output from the PD 160 into an output signal (e.g. a PWM signal) corresponding to a dust concentration, and output the converted signal through the connector pin 126. Since the circuit portion has a similar structure to that of the known dust sensor 1, the detailed description thereof will be omitted.

The circuit portion of the PCB 125 of the known dust sensor 1 includes a voltage regulation portion which applies a proper voltage to the LED 130. However, the dust sensor 100 of the present invention may be configured such that a microcomputer included in the circuit portion of the PCB 125 controls the voltage applied the LED 130 through the voltage regulation portion according to the correction control signal output from the controller.

Meanwhile, external light blockages for preventing introduction of external light may be installed to both end openings 101a and 101b of the air passage 101 in the dust sensor 100.

In the dust sensor 100 of the present invention, both end openings 101a and 101b of the air passage 101 are portions through which air and dust contained therein are introduced into the sensor. Therefore, external light may be easily introduced through the above portions.

In particular, sunlight or living light such as illumination around vehicles, or light, such as head lamp light of opposite vehicles or surrounding vehicles, may be introduced into the sensor through the both end openings 101a and 101b of the air passage 101.

Since the external light introduced into the air passage 101 of the dust sensor 100 acts as disturbance light when the sensor detects the concentration of dust, the dust sensor 100 may malfunction (cause erroneous detection) due to the external light.

Figure 6:
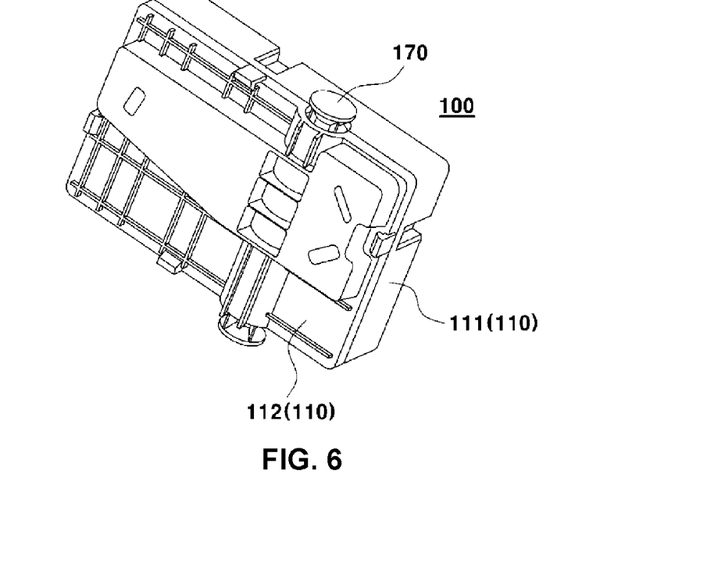
FIG. 6, FIG. 7, FIG. 8, and FIG. 9 are views illustrating a state in which external light blockages are installed to both end openings of an air passage in various embodiments of the present invention.
Figure 7:
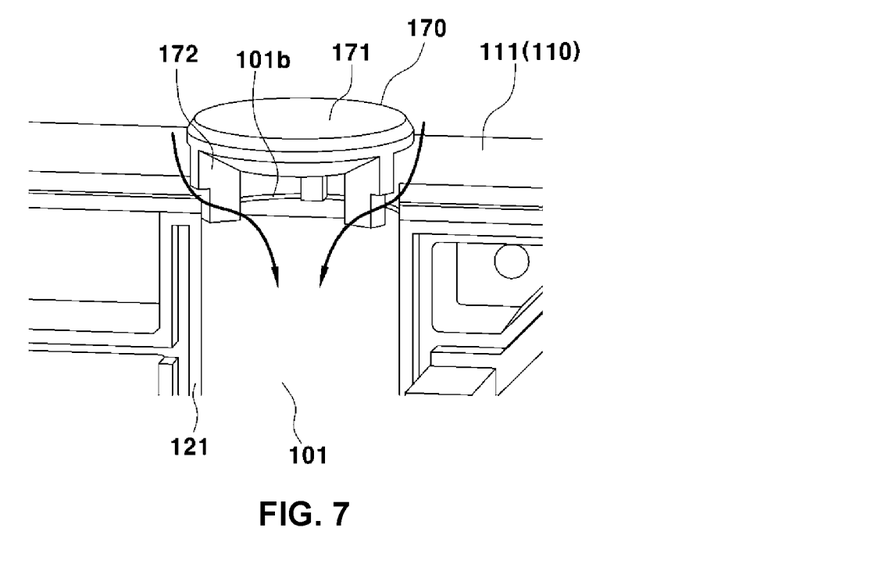

Accordingly, the external light blockages for preventing introduction of external light may be installed to both end openings 101a and 101b of the air passage 101. As an example, light-blocking caps 170 for blocking external light may be installed to both end openings 101a and 101b of the air passage 101, as illustrated in FIGS. 6 and 7.

Each of the light-blocking caps 170 may be formed and installed so as to block light while having a passage for introduction of dust and air. The light-blocking cap 170 is disposed so as to be spaced apart from the associated opening 101a or 101b of the air passage 101, and may include a blockage plate 171 disposed to cover the associated opening 101a or 101b of the air passage 101, and a plurality of pillars 172 which are integrally or monolithically formed in the blockage plate 171 and support the blockage plate 171 in the state in which the blockage plate 171 is spaced apart from the opening 101a or 101b of the air passage 101.

In this case, the blockage plate 171 may have a circular plate shape (a disk shape), and the pillars 172 may be formed so as to be circumferentially spaced around the blockage plate 171.

In addition, the overall position of the light-blocking cap 170 including the blockage plate 171 may be fixed by press-fitting the ends of the pillars 172 into the associated opening 101a or 101b of the air passage 101.

In this case, the space between the opening 101a or 101b of the air passage 101 and the blockage plate 171, and the space between one pillar 172 and another pillar 172 are provided as passages for introduction of dust and air.

As such, when the light-blocking caps 170 having the blockage plate 171 is installed at each of both end openings 101a and 101b of the air passage 101, external light may not be introduced into the air passage 101 through both end openings 101a and 101b, but only dust and air may be introduced into the air passage 101.

Consequently, infrared light introduced from the outside may pass through the infrared-passing filter 150 even though the infrared-passing filter 150 installed in the second light passage 103 blocks ultraviolet light and visible light. However, when the above separate external light blockages (light-blocking caps) are installed to both end openings 101a and 101b of the air passage 101, all of external light including infrared light may be blocked. Therefore, it is possible to effectively prevent the dust sensor 100 from malfunction due to the introduction of external light.

Figure 8:
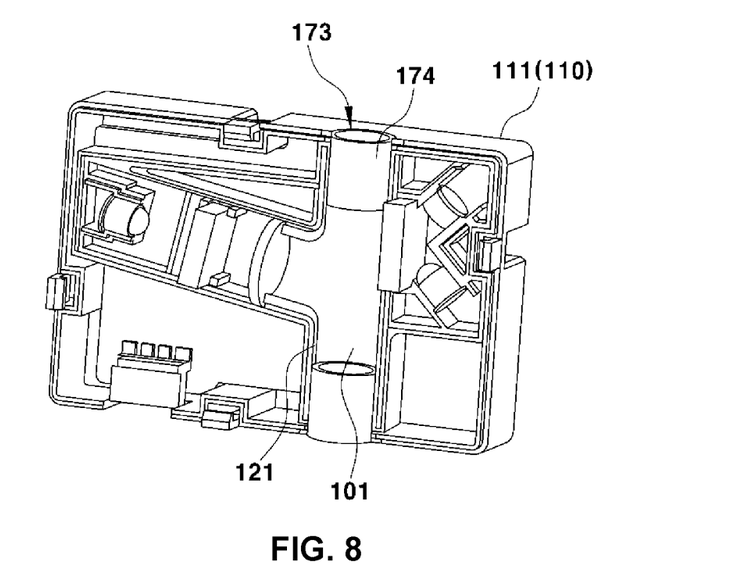
Figure 9:
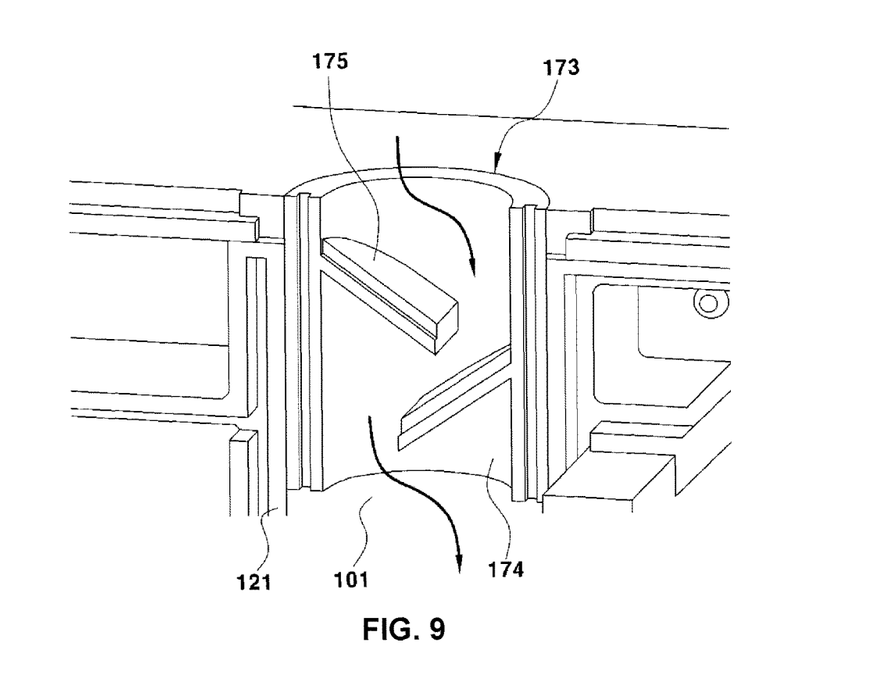

Meanwhile, FIGS. 8 and 9 illustrate an example in which separate external light blockages 173 having shield walls 175 are inserted into and installed to both ends of the air passage 101.

As illustrated in the drawings, each of the separate external light blockages 173 includes a tubular body 174 which is inserted into and installed to the end of the air passage such that the outer surface of the tubular body 174 comes into contact with the inner surface of the air passage 101, and a plurality of shield walls 175 which are fixedly disposed in opposite sides on the inner surface of the tubular body 174 so as to form a passage for introduction of dust and air in a zigzag form while blocking light.

In this case, each of the shield walls 175 may be a wall which is obliquely installed on the inner surface of the tubular body 174, and the shield walls 175 are installed at predetermined intervals in the longitudinal direction of the air passage 101 so as to form a cross structure.

In order for the shield walls 175 to have a cross structure, the end of each shield wall 175 separated from the inner surface of the body 174 is located over the center of the body 174 on the transverse cross-section thereof.

In addition, when the air passage 101 is a circular passage in section, the body 174 may be a circular tubular body, and each of the shield walls 175 may have a substantially semicircular shape.

The external light blockages 173 are installed at both ends of the air passage 101 in the sensor so as to introduce only dust and air through both end openings 101a and 101b of the air passage 101 and at the same time to block external light through the shield walls 175.

Figure 10:
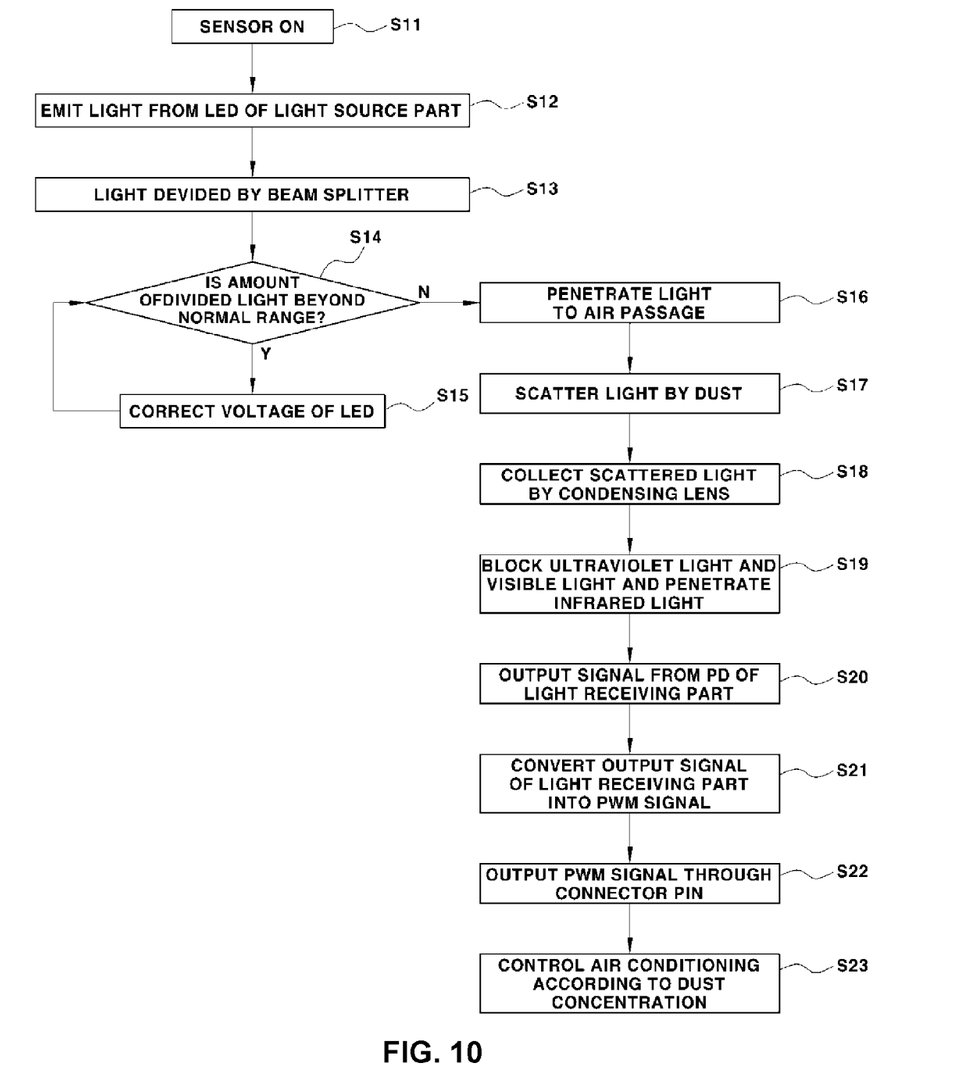
FIG. 10 is a flowchart illustrating a dust detection process using the dust sensor according to various embodiments of the present invention.

The configuration of the vehicular dust sensor according to various embodiments of the present invention has been described above, and a dust detection process using the dust sensor will be described below with reference to FIG. 10.

As illustrated in the drawing, the LED 130 of the light source module is operated when the sensor is turned on (S11), thereby emitting light (S12). The light emitted from the LED 130 is divided by the beam splitter 131, and a portion thereof is detected by the light sensor 132 (S13).

In this case, the controller (e.g. the air conditioning controller 200 in FIG. 2) receives a signal output from the light sensor (the PD) 132 and determines whether the amount of the light divided by the beam splitter 131, i.e. the amount of spectral light is in a normal range (S14). When the amount of spectral light is beyond the normal range, the controller outputs a control signal for correcting the voltage applied to the LED such that the amount of spectral light is in the normal range.

The circuit portion of the dust sensor 100 corrects the voltage applied to the LED 130 in response to the control signal of the controller (S15). Then, when the amount of spectral light is in the normal range, the controller uses a signal (e.g. a PWM signal) output from the dust sensor in order to determine the concentration of dust in air.

That is, when the amount of spectral light is in the normal range, light, which is emitted from the LED 130 and then passes through the beam splitter 131, is radiated to the illumination region of the air passage 101 (S16). The light radiated to the illumination region is scattered by dust in the air passage 101 (S17), and is then collected by the condensing lens 140 (S18).

In addition, only infrared light in the light collected by the condensing lens 140 passes through the infrared-passing filter 150, and is input to the PD 160 of the light receiving module (S19). The PD 160 outputs an electric signal corresponding to the amount of scattered light (S20).

Here, the circuit portion of the PCB 125 converts the signal output from the PD 160 into an output signal, e.g. a PWM signal, corresponding to the concentration of dust in air (S21). The PWM signal is an output signal of the dust sensor, and is output from the dust sensor 100 through the connector pin 126 to be input to the controller (S22).

Thus, the controller (air conditioning controller) performs air conditioning control according to the dust concentration, based on the signal output from the dust sensor 100, and particularly performs the fixed air conditioning control in order to remove dust in the vehicle interior, based on the dust concentration as necessary (S23).

As is apparent from the above description, a vehicular dust sensor according to various embodiments of the present invention has the following effects.

The sensor includes a linear air passage which passes air and dust therethrough, thereby enabling dust introduced into the sensor to be easily discharged. Therefore, it is possible to effectively prevent dust deposition in the sensor and lens contamination due to dust, and to prevent sensor performance deterioration caused by the dust deposition or the contamination.

An infrared LED is used as a light emitting element, and an infrared-passing filter is installed between a PD as a light receiving element and a condensing lens. Therefore, it is possible to reduce the influence of external light introduced from the outside of the sensor.

Since external light blockages, which pass only air and dust therethrough and block external light, are installed at both end inlet/outlet (openings) of the air passage for the introduction and pass of dust, it is possible to effectively prevent the sensor from malfunction due to the introduction of external light.

The light emitted from the LED is divided by a beam splitter, the divided light (spectral light) is detected by a separate light sensor, and output correction is automatically performed based on the detected signal by the light sensor when the light output from the LED is abnormal. Therefore, it is possible to more improve the reliability of sensor performance.

For convenience in explanation and accurate definition in the appended claims, the terms "upper" or "lower", "inner" or "outer" and etc. are used to describe features of the exemplary embodiments with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A vehicular dust sensor comprising:
   a case having an inner space;
   a light source module disposed in the inner space of the case, and irradiating an air passage with light, the air passage being provided in the light source module for introduction and pass of air and dust;
   a condensing lens to collect light, emitted from the light source module and scattered by dust in air in the air passage;
   a light receiving module receiving the scattered light collected by the condensing lens to output an electric signal corresponding to a dust concentration; and
   an inner housing disposed in the inner space of the case to form the air passage,
   external light blockages which block introduction of external light while passing the air and the dust therethrough, and are disposed to both end openings of the air passage as entry ports for the air and the dust,
   wherein each of the external light blockages comprises:
      a tubular body inserted into and disposed to each of the both end openings of the air passage such that an outer surface of the tubular body comes into contact with an inner surface of the air passage; and
      shield walls fixedly disposed on an inner surface of the tubular body to form a passage for introduction of the dust and the air while blocking the external light, and
   wherein the shield walls are fixedly disposed in opposite sides on the inner surface of the tubular body to form the passage for introduction of the dust and the air in a zigzag form while blocking the external light, and are disposed at intervals in a longitudinal direction of the air passage to form a cross structure.

2. The vehicular dust sensor of claim 1, wherein the air passage is a linear air passage formed such that the air and the dust are introduced into and easily discharged from the linear air passage, and both end openings of the linear air passage are entry ports for introduction and discharge of the air and the dust.

3. The vehicular dust sensor of claim 1, wherein the air passage is a passage having a constant cross-sectional shape.

4. The vehicular dust sensor of claim 3, wherein the air passage is a passage having a circular cross-sectional shape.

5. The vehicular dust sensor of claim 1, wherein the light source module is an infrared light source module to emit infrared light, and an infrared-passing filter is disposed between the condensing lens and the light receiving part.

6. The vehicular dust sensor of claim 1, wherein the inner housing is formed with a groove-shaped air guide portion for forming the air passage, and an inner surface of one side portion of the case is formed with a groove-shaped linear air guide portion for forming the air passage in a combined state with the air guide portion of the inner housing.

7. The vehicular dust sensor of claim 1, wherein a first light passage having a structure that is branched from the air passage by the inner housing is formed, and a light emitting element of the light source module is disposed in the first light passage, so that the light emitting element irradiates the air passage with light through the first light passage.

8. The vehicular dust sensor of claim 1, wherein a second light passage having a structure that is branched from the air passage by the inner housing is formed, and a light receiving element of the light receiving module and the condensing lens are disposed in the second light passage, so that light scattered in the air passage is collected by the condensing lens while passing through the second light passage, and is then input to the light receiving element.

9. The vehicular dust sensor of claim 1, wherein
a beam splitter, which divides at least a portion of light emitted from a light emitting element of the light source module and passes the remainder of light therethrough to irradiate the air passage, and a light sensor, which detects the light divided by the beam splitter to output an electric signal according to an amount of the divided light, are disposed in front of the light emitting element of the light source part; and
a controller determines whether light output from the light emitting element is abnormal based on the signal output from the light sensor.

10. The vehicular dust sensor of claim 9, wherein the light sensor comprises a photo diode which receives the divided light to output an electric signal.

11. The vehicular dust sensor of claim 9, wherein
when the amount of the light divided by the beam splitter is beyond a predetermined normal range, the controller determines that the light output from the light emitting element is abnormal based on the signal output from the light sensor; and
the controller regulates a voltage applied to the light emitting element such that the amount of the light divided by the beam splitter is in the normal range, and controls the light output from the light emitting element.

12. The vehicular dust sensor of claim 1, wherein each of the shield walls is obliquely disposed on the inner surface of the tubular body.

13. The vehicular dust sensor of claim 1, wherein the air passage is a circular cross-sectional passage, and the tubular body has a circular tubular shape, and each of the shield walls has a semicircular shape.

* * * * *